(12) United States Patent
Lucht et al.

(10) Patent No.: US 6,706,218 B2
(45) Date of Patent: Mar. 16, 2004

(54) THERMOCHROMIC POLYMERS FOR RAPID VISUAL ASSESSMENT OF TEMPERATURE

(75) Inventors: Brett L. Lucht, Wakefield, RI (US); William B. Euler, Narragansett, RI (US); Otto J. Gregory, Wakefield, RI (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 311 days.

(21) Appl. No.: 09/758,075

(22) Filed: Jan. 10, 2001

(65) Prior Publication Data

US 2002/0149003 A1 Oct. 17, 2002

Related U.S. Application Data

(60) Provisional application No. 60/202,161, filed on May 4, 2000, and provisional application No. 60/175,487, filed on Jan. 11, 2000.

(51) Int. Cl.$^7$ .......................... G01N 31/22; G01K 11/16
(52) U.S. Cl. .................... 252/408.1; 116/201; 116/207; 374/162
(58) Field of Search ...................... 252/408.1; 116/201, 116/207; 374/162

(56) References Cited

U.S. PATENT DOCUMENTS

| | | | | |
|---|---|---|---|---|
| 4,156,365 A | * | 5/1979 | Heinmets et al. | |
| 4,912,203 A | | 3/1990 | Kluger et al. | |
| 4,959,430 A | | 9/1990 | Jonas et al. | |
| 5,053,339 A | | 10/1991 | Patel | |
| 5,085,607 A | | 2/1992 | Shibahashi et al. | ........... 446/14 |
| 5,266,677 A | | 11/1993 | Samulski et al. | |
| 5,279,768 A | | 1/1994 | Destryker et al. | |
| 5,420,224 A | | 5/1995 | Samulski et al. | |
| 5,503,583 A | | 4/1996 | Hippely et al. | ............... 446/14 |
| 5,527,434 A | | 6/1996 | Hamnett et al. | |
| 5,569,708 A | | 10/1996 | Wudl et al. | |
| 5,806,528 A | | 9/1998 | Magliochetti | |

FOREIGN PATENT DOCUMENTS

| | | | |
|---|---|---|---|
| ES | 2158764 A1 | * | 9/2001 |
| JP | 04168188 A | * | 6/1992 |
| JP | WO00/53659 | | 9/2000 |

OTHER PUBLICATIONS

Roux, Claudine; Faid, Karim; Leclerc, Mario. "Polythiophene Derivatives: Smart Materials." Polymer News. 1994. vol. 19, pp. 6–10, especially pp. 8–10.
Polymers for Displays, IBM Technical Disclosure Bulletin, Oct. 1983, p. 2503.
A Phenomenological Model for Predicting Thermochromism of Regioregular and Nonregioregular Poly(3–alkylthiophenes), Cheng Yang, et al. American Chemical Society, 1996, pp. 6510–6517.
Thermochromic Properties of Polythiophenes: Oligomers vs Polymers, Karim Faid et al., J. Chem. Soc., Chem. Commun., 1993, pp. 962–963.
Thermochromic properties of quaterthiophene, an alkyl–substituted quaterthiophene derivative and its corresponding polymer, Nicolas DiCesare et al., Chemical Physics Letters 291, 1998, pp. 487–495.
Thermochromic and solvatochromic effects in Poly(3–hexylthiophene), O. Inganas, et al., Synthetic Metals, 22, 1988, pp. 395–406.
Thermochromic properties of polythiophenes: structural aspects, Claudine Roux, et al., Makromol. Chem., 194, 1993, pp. 868–877.
Chromism of Soluble Polythienylenes, S.D.D.V. Rughooputh, et al., Journal of Polymer Science: Part B: Polymer Physics, vol. 25, 1987, pp. 1071–1078.
Chromic Phenomena in Regioregular and Nonregioregular Polythiophene Derivatives, Karim Faid, et al., Chem. Mater., 1995, 7, pp. 1390–1396.
Structure and thermochromic solid–state phase transition of poly(3–alkylthiophene): [3] effects of alkyl side chain length on the phase transitional behavior, Kohji Tashiro et al., Synthetic Metals, 55–57, 1993, pp. 321–328.
Thermochromism in poly(3–alkylthiophenes) and their polymer blends, O. Inganas, et al., Synthetic Metals, 37, 1990, pp. 195–205.
Thermochromism of poly(substituted thiophene) with urethane bond and its application to reversible thermal recording, Nobuaki Hirota, et al., Synthetic Metals, 80, 1996, pp. 67–72.
Polythiophenes—Electrically Conductive Polymers, G. Schopf et al., 129.
Towards a theoretical design of thermochromic polythiophenes, Nicolas Di Cesare, et al., Chemical Physics Letters 275, 1997, pp. 553–539.
Optical absorption in polythiophene as a function of temperature, Bjorn Magnusson, Master's Thesis, pp. 1–38.

* cited by examiner

*Primary Examiner*—Elizabeth McKane
(74) *Attorney, Agent, or Firm*—Samuels Gauthier & Stevens

(57) ABSTRACT

A thermochromic polymer-based temperature indicator composition which comprises a polythiophene and a carrier medium. The composition is characterized in that the polythiophene is present in the medium in an amount of about 0.05 to about 5.0% by weight based on the total weight of the composition. The structure of the compound is designed such that when the composition is placed in a heat-exchange relationship with an article, the composition will exhibit a color change when a design temperature or a temperature beyond the design temperature is reached in the article.

21 Claims, 3 Drawing Sheets

THERMOCHROMIC POLYMERS FOR RAPID VISUAL ASSESSMENT OF TEMPERATURE

CROSS-REFERENCE TO RELATED APPLICATIONS

This application claims the benefit of U.S. Provisional Application No. 60/175,487 filed on Jan. 11, 2000 and U.S. Provisional Application No. 60/202,161 filed on May 4, 2000.

BACKGROUND OF THE INVENTION

1. Field of the Invention

The invention relates to polythiophene-based temperature indicators.

2. Description of Relevant Art

Polythiophenes are known for their electrically conductive properties. One technique used to study the electron flow is to analyze associated color changes when the temperature of the polythiophene is varied. Color changes provide insight into the electro-conductive properties of the polymer. There are numerous patent and literature citations which describe this work.

In many instances it is clearly desirable to know when an object or article reaches or has exceeded a specific temperature simply by viewing the object and noting that at least a portion of the object has exhibited a color change. Viewing includes visual observation by an individual or detection of color change by a sensor, which sensor would output a signal to be detected in any suitable manner.

As an example, in the food service industry there are hot trays and cold trays in which food is stored and/or served. If a cold tray, such as by regulation, is required to be maintained at a temperature of 38° or lower then a sensor system might be in place to signal (alarm) that the temperature is above 38° F. Alternatively, a thermometer might be used. However, in the food service industry, margins are thin, and unless required by regulation, sensing systems will not be used. There are enumerable situations where it would be desirable to provide a visual color indicator which would appear on an article if the temperature were unsafe, hot drink cups, stove tops, etcetera and/or not functioning properly, hot plates, freezers, etcetera, or if to know when desired temperatures were reached, e.g. ovens.

BRIEF SUMMARY OF THE INVENTION

The present invention utilizes the color change characteristics of polythiophenes in a sensing system, which system will change color at a specific design temperature.

The polythiophene is generally of the structure:

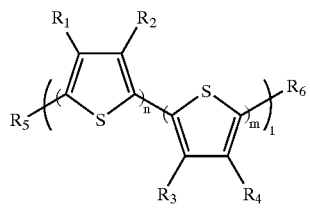

I wherein $R_1$–$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted heteroaryl or substituted or unsubstituted aryl radical n is between 1 and 1000,
m is between 0 and 1000, and
l is between 1 and 1000.

The synthesized polythiophene is mixed with a carrier system or liquid medium. Depending upon the specific polythiophene used, the carrier system can be aqueous or organic. The polythiophene can be used in the carrier system as a mechanical separation, colloidial solution, or a molecular solution. Also, surfactants, anionic, cationic or non-anionic, can be used if necessary in the carrier system to ensure uniform distribution of the polythiophene in the system.

For the example described in the Background, a polythiophene is synthesized to exhibit the color change at about 38° F. and maintain that color change at lower temperatures when used in a carrier system, which system is placed in heat transfer relationship with the tray (article) the temperature of which is being monitored. Conversely, if the hot tray is to be maintained at about 180° F. or higher then a polythiophene is synthesized to change color at about 180° F. The polythiophene is mixed in a carrier system, which carrier system is placed in heat exchange relationship, such as by coating, at least a portion of the tray.

In a preferred embodiment, polythiophene in an amount of 0.05 to 5.0% by weight based on the total weight of the system, preferably 0.2 to 0.8% weight, is mixed with an organic solvent. Suitable solvents include tetrahydrofuran, chloroform, methylene chloride, toluene, and N-methylpyrrolidone.

The system is generally applied to the article as a coating on an area of the article, or the entire article, which will be visible during the expected use of the article. The coating can be applied by any technique known in the art, such as by brush, roller, spraying, etc. Accordingly, the coatings typically have a thickness of 0.1 to 1000 microns. The carrier system can also be absorbed on a surface or both absorbed and adsorbed on a surface.

In another aspect of the invention, the system is comprised of polythiophenes that visually and reversibly change color at a prescribed temperature in the range of about –40–180° C. and are thermally stable to high temperatures in a range of about 200–300° C. The temperature of the color change of the polythiophenes, hereinafter the thermochromic transition, and the high and low temperature colors can be tailored by chemical modification of the polythiophenes.

In synthesizing a polythiophene for a specific design temperature, eg. for the series of poly(3-alkylthiophene)s there is roughly an inverse correlation with the length of the n-alkane substituent and the temperature of the thermochromic transition for both the regiorandom ($R_1$=alkyl, $R_4$=alkyl, n≅0.8, m≅0.2, l=40–80, $R_2$, $R_3$, $R_5$, $R_6$=H) and regioregular ($R_1$=alkyl, n=40–80, m=0, $R_2$, $R_5$, $R_6$=H), poly(3-n-alkylthiophene)s. For regiorandom polymers longer substituents such as n-hexadecyl have lower temperature thermochromic transitions (81° C.) than shorter chain substituents such as n-octyl (130° C.). The regioregular polymers have higher thermochromic transitions than the regioregular polymers but the same inverse correlation with chainlength is observed. The n-hexadecyl and n-octyl have thermochromic transition centered around 125 and 175° C. As long as the number of thiophene units in the polymer is approximately greater than sixteen the thermochromic transitions is molecular weight independent. Oligothiophenes (n+m+1<16) have lower temperature thermochromic transitions than the polythiophenes (n+m+1>16).

Yet another aspect of the invention comprises paint, plastic or rubber composites comprised of the polythiophenes that are one color at temperatures below the thermochromic transition and are another color while above the transition. Both the low and high temperature colors and the temperature of the color change vary as a function of the substituent groups $R_1$, $R_2$, $R_3$, $R_4$, $R_5$, and $R_6$, the number of repeat units (1), and regioregularity of the repeat units (n and m).

The invention also comprises polythiophenes that can be used as pure compounds or can be incorporated into paints including polyurethanes, polysiloxanes, polyacrylates, and other related polymer-based paints and coatings with about 0.5% polymer based pigment with retention of the thermochromic behavior. The thermochromic polymer-based pigments can be incorporated via injection molding or extrusion into many commercially important plastics such as poly (ethylene terephthalate) (PET), polysytrene, polyethylene (HDPE and LDPE), other polyolefins, polydienes, polycarbonates, polyacrylics, polyacrylic acids, polyacrylamides, polymethacrylics, polyvinyl ethers, polyvinyl halides, poly(vinyl nitrile)s poly vinyl esters, polyesters, polysofones, polysulfonamides, polyamides, polyimines, polyimides, carbohydrates, and polymer mixtures and copolymers. The plastics retain a visually retrievable thermochromic response with pigment loadings of about 0.5% polymer-based pigment.

The sensor system can be used as a safety feature or a thermal sensor for stoves, baking utensils or pans, radiator caps, cooling racks, paper/plastic coffee cups and lids, baby bottles, cooking utensils, cooking ware, fire safety, food packaging, instrument sterilization, novelty items, food preparation and handling equipment, warning labels, packaging film, microwave dishes, frozen food packages, beverage bottles, cable or wire coverings, motor and engine parts, breaking systems, automobile or truck tires, bathtub coatings, and other substrates and/or articles where a visual indication of a temperature change is important.

BRIEF DESCRIPTION OF THE DRAWING(S)

DESCRIPTION OF THE PREFERRED EMBODIMENT(S)

Figure 1:
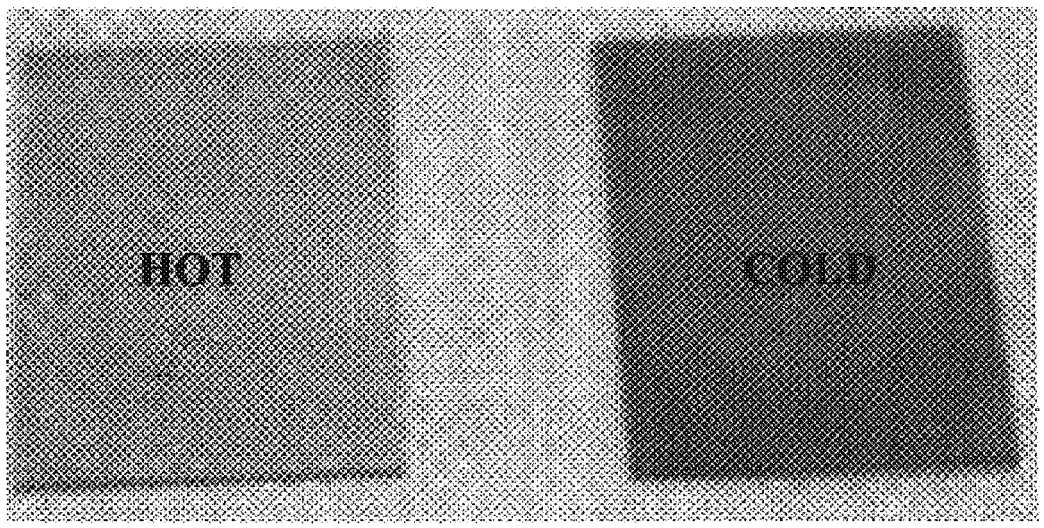
FIG. 1 is a photograph depicting a polythiophene film of the invention on glass, hot and cold.

Referring to FIG. 1, a photograph of two films is depicted, one at room temperature and one above the thermochromic transition. The films are comprised of a polythiophene wherein $R_1$ and $R_4$ are —$(CH_2)_{17}CH_3$, $R_2$, $R_3$, $R_5$ and $R_6$ are H, n is 0.8, m is 0.2, and 1 is between 40 and 80. The film changes color at about 60° C.

Figure 2:
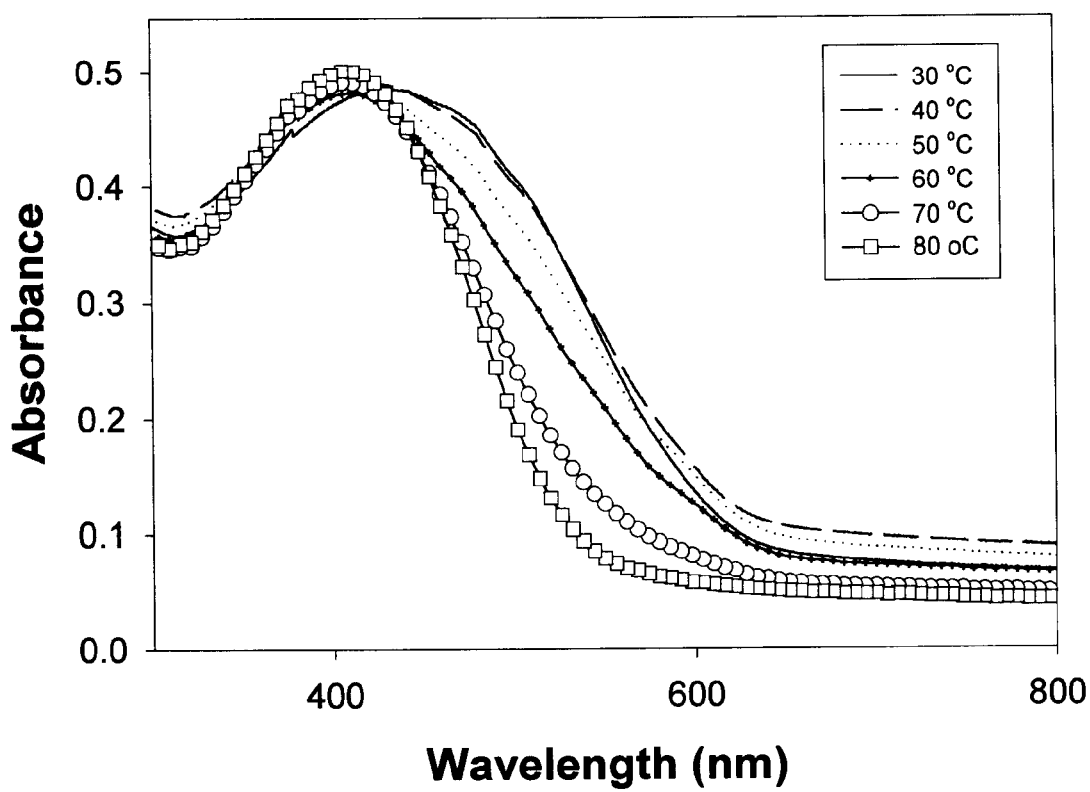
FIG. 2 is a graph depicting the visible spectrum of a polythiophene film of the invention as a function of temperature.

Referring to FIG. 2, a graph of the visible spectrum of a polythiophene wherein $R_1=R_4=$—$(CH_2)_{17}CH_3$, $R_2=R_3=R_5=R_6=H$ as a function of temperature is shown. The graph displays a dramatic difference in absorption around 500 nm. At low temperature the absorbance is quite high while at high temperature the absorbance is low. This feature in the optical spectrum is responsible for the visual color change of the polythiophene.

Figure 3:
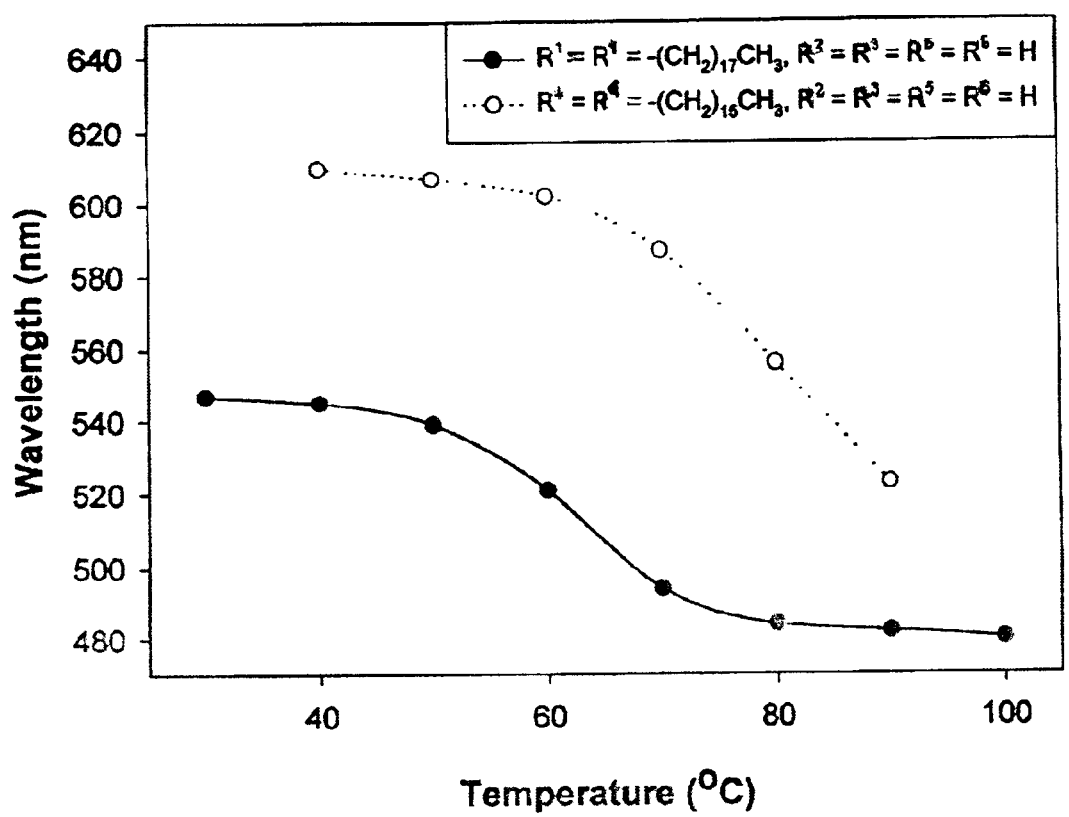
FIG. 3 is a graph depicting a plot of the wavelength of the absorption band edge at half the maximum intensity for a polythiophene as a function of temperature.

Referring to FIG. 3, a plot of the wavelength of the absorption band edge at half of the maximum intensity for a polythiophene as a function of temperature is shown. The inversion point for the color transition for the polythiophene wherein $R_1=R_4=$—$(CH_2)_{17}CH_3$, $R_2=R_3=R_5=R_6=H$ occurs at about 62° C. while the inversion point for the color transition for the polythiophene wherein $R_1=R_4=$—$(CH_2)_{15}CH_3$, $R_2=R_3=R_5=R_6=H$ occurs at 81° C. This indicates that the temperature of the thermochromic transition can be changed by altering the substituents on the polymer backbone.

Based on the teachings of this disclosure, one skilled in the art could design a polythiophene with a predetermined thermochromic transition by investigating the systematic trends of the thermochromic transition as a function of polythiophene or oligothiophene structure. The temperature can be dropped by increasing the length of the alkyl substituent $R_1$ or by via the preparation of oligmers. The temperature of the thermochromic transition can be increased by preparing regioregular poly(3-alkylthiophene)s or using shorter alkylsubstituents ($R_1$).)

The invention will further be described with reference to following non-limiting examples.

Preparation of Poly(3-alkylthiophene)s

3-n-octadecylthiophene 3-n-octadecylthiophene was prepared as set forth in Kumda et al *Bull. Chem Soc. Jpn.* 1976, 49, 1958–1969 and Tetrahedron 1982, 38, 3347–3354. A dry 1000 mL 2 neck flask was charged with Mg ribbon (3.34 g, 137 mmol) under $N_2$ followed by addition of ~200 mL of anhydrous $Et_2O$. The flask was cooled in an ice bath (0° C.). In a separate 500 mL flask 40 g (120 mmol) of n-$C_{18}H_{37}Br$ was dissolved in ~200 mL of anhydrous $Et_2O$ under $N_2$. The $Et_2O$ solution of n-$C_{18}H_{37}Br$ was slowly transfer into the flask containing the Mg ribbon, with sonication, stirring, and addition of $I_2$ to initiate Grignard. After complete addition of n-$C_{18}H_{37}Br$ to the Mg the reaction mixture was allowed to stir overnight to allow for complete formation of the Grignard reagent (n-$C_{18}H_{37}MgBr$). A dry 1000 mL 3-neck flask was charged with 0.540 g of 1,3-Bis(diphenylphosphino)propane nickel (II) chloride was added under nitrogen followed by ~100 mL of anhydrous $Et_2O$ and 11.25 mL (120 mmol) of 3-bromothiphene. The flask was then cooled in an ice bath (0° C.). The $Et_2O$ solution of n-$C_{18}H_{37}MgBr$ was slowly added to the flask containing the nickel catalyst and the 3-bromothiophene to prevent the generation of excessive heat and high concentrations of n-$C_{18}H_{37}MgBr$ in the presence of the catalyst. The reaction mixture was allowed to stir overnight resulting in the formation of two layers. The top $Et_2O$ layer contained the product and the second small lower dark brown oily layer contained the Ni catalyst and the Mg salts. The primary side product of the reaction was the coupling product of two equivalents of n-$C_{18}H_{37}MgBr$ to form $C_{36}H_{74}$, which was easily separated form the product since it had low solubility in $Et_2O$. The product was purified via aqueous workup followed by filtration and removal of the $Et_2O$ by rotoevaporation to leave the impure low melting solid product. This solid was redissolved in a minimal amount of $Et_2O$ (~30 mL) followed by addition of ~250 mL of MeOH and placed into low temperature freezer (−80° C.) for recrystalization. The yield of this reaction is about 80–90%.

Poly(3-n-ocatdecylthiophene)

Poly(3-n-ocatdecylthiophene) was prepared as forth in Leclerc et. al. *Makromol. Chem.* 1989, 190, 3105–3116.

3-ocatadecylthiophene (10 g, 30 mmol) was added to a dry 500 mL round bottom flask under $N_2$ and dissolved in 100 mL of $CHCl_3$. In a separate dry 500 mL flask under $N_2$ was added $FeCl_3$ (24.3 g, 90 mmol) and 100 mL of $CHCl_3$. The $CHCl_3$ solution of 3-ocatadecylthiophene was slowly transferred to the flask containing the $FeCl_3$ resulting in the generation of heat. The contents of the flask were stirred at RT for 24–36 h. The reaction mixture was then slowly dripped into rapidly stirring MeOH (1 L) resulting in the precipitation of the polymer. The precipitate was collected via vacuum filtration, washed with MeOH (100 mL) and redissolved in 150 mL of $CHCl_3$ with the assistance of sonication. The solution was washed/reduced with aqueous hydrazine (2×100 mL, 0.5 M) and aqueous HCl (2×100 mL, 0.5 M). The organic layer was slowly dripped into of rapidly stirring MeOH (1 L) to reprecipitate the polymer which was collected by vacuum filtration.

One skilled in the art would recognize that other known methods only precipitate the polymer once and reduce/purify the polymer via Sohxlet extraction with MeOH. Further, it will be apparent to one skilled in the art that the polymerization reaction can be carried out in methylene chloride as opposed to chloroform if it would be more economical or EPA acceptable.

Development of Thermochromic Paints

Scheme 1

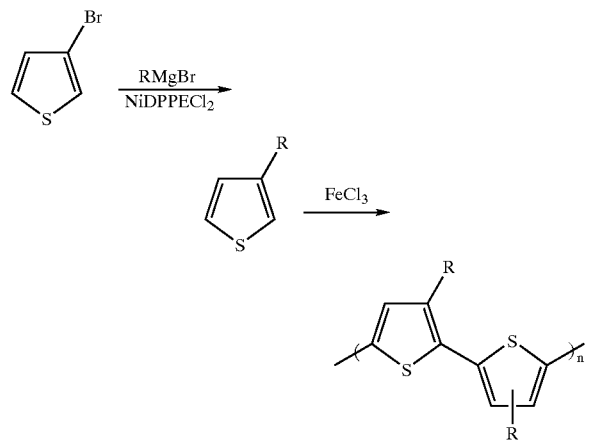

50 mg of poly (3-octadecylthiophene) prepared via the procedure shown in Scheme 1, where $R=C_{18}C_{37}$ was dissolved in 2.0 ml of tetrahydrofuran. This deeply colored solution was added to 25 ml of Minwax fast drying polyurethane (clear semi-gloss). This provides a uniform mixture that was applied to paper, plastic, and painted metal surfaces. Upon drying (20 min) the surfaces where heated to 100° C. for 1 min to remove any residual solvent from the coating and then allowed to cool to room temperature. After cooling to room temperature the "painted" surfaces are red. When the red surfaces are heated above 60–70° C. the color of the surfaces changes from red to yellow. The color change is accompanied by a change in the visual transparency of the surface coating. When the red coating is opaque while when yellow the coating is translucent. This process is very similar to what is observed for the pure poly (3-octadecylthiophene). The coating adheres strongly to paper, plastic, and painted metal surfaces. Addition of blue pigments such as ultramarine blue allow adjustment of the cold and hot colors. The color can be adjusted to a gray/purple when cold and bright green when hot. The thermo chromic paints can be applied in various manners including brush, sponge, roller, and airbrush.

Scheme 2

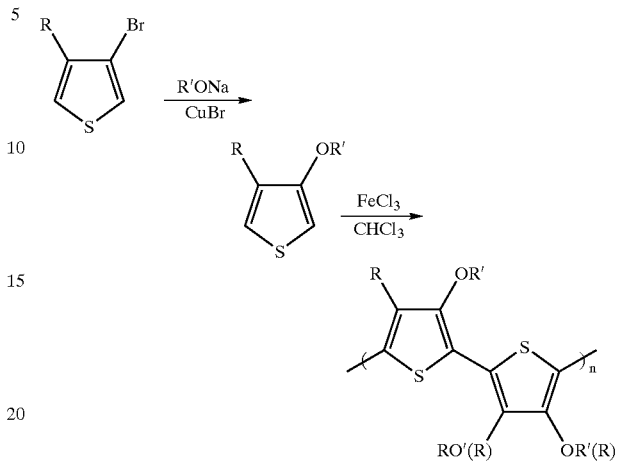

Non-regioregular 3-alkoxy-4-alkyl substituted polythiophenes for thermochromic applications have been synthesized according to Scheme 2, where $R=CH_3$ and $R'=C_{18}H_{37}$. These polymers can be used as a reversible thermal sensor that detects excursion through a single temperature with visual or optical detection. At temperatures below the thermochromic transition polymer films are violet, above the transition the films are orange. The temperature of the thermochromic transition can be adjusted by variation of the backbone alkyl or alkoxy substituents.

All of the polythiophene-based pigments described herein, most particularly 3-alkylpolythiophenes and 3-alkoxy-4-alkylpolythiophenes, can be incorporated into polymer based-paints such as polyurethanes and polysiloxanes or plastics and retain the thermochromic behavior. Upon incorporation of the thermochromic polymer based pigments into plastics the materials have been determined to be viable for FDA approval.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method of detecting when an article meets or exceeds a specific temperature which comprises:

treating at least a portion of the article with a composition comprised of a compound having the following structure:

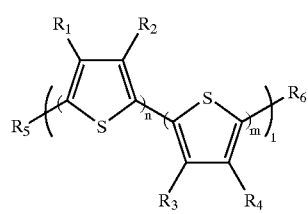

I wherein $R_1$–$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted heteroaryl or substituted or unsubstituted aryl radical, n is between 1 and 1000,
m is between 0 and 1000, and
1 is between 1 and 1000; and a carrier medium, the compound having a low temperature color and present in the medium in an amount of about 0.05 to about 5.0% by weight based on the total weight of the composition, the structure of the compound designed such that when the composition is placed in a heat-exchange relationship with the article, the low temperature color will change to a high temperature color when the specific temperature is met or exceeded in the article; the change of the low temperature color to the high temperature color commencing within plus or minus 5–10° C. below the specific temperature; and detecting when the article has met or exceeded the specific temperature.

2. The method of claim 1 wherein treating comprises brushing.

3. The method of claim 1 wherein treating comprises rolling.

4. The method of claim 1 wherein treating comprises spraying.

5. The method of claim 1 wherein treating comprises admixing the composition with at least a portion of the article.

6. The method of claim 1 wherein treating comprises coating at least a portion of the article.

7. The method of claim 1 wherein treating comprises coating at least a portion of the article and admixing the composition with at least a portion of the article.

8. The method of claim 1 wherein the specific temperature of the composition is in the range of between −40 to 180° C.

9. The method of claim 8 wherein the selected temperature of the composition is any selected temperature within the range.

10. The method of claim 1 wherein the medium is selected from the group consisting of polyurethanes; elastomers including polysiloxanes and polydienes; polyacrylates, poly(ethylene terephthalate)s (PET), polysytrenes, polyolefins including polyethylenes (HDPE and LDPE) and polypropylene, polycarbonates, polyacrylics, polyacrylic acids, polyacrylamides, polymethacrylics, polyvinyl ethers, polyvinyl halides, poly(vinyl nitrile)s polyvinyl esters, polyesters, polysofones, polysulfonamides, polyamides, polyimines, polyimides, and carbohydrates.

11. The method of claim 1 wherein $R_1$ and $R_4$ are —$(CH_2)_{17}CH_3$, $R_2$, $R_3$, $R_5$, and $R_6$ are H, n is 0.8, m is 0.2, and 1 is between 40 and 80, the composition characterized in that the low temperature color is red a the high temperature color is yellow, and the specific temperature is about 60° C.

12. The method of claim 1 wherein the compound is present in the medium in an amount of about 0.5% by weight based on the total weight of the composition.

13. A thermochromic polymer-based temperature indicator composition which exhibits a color change when the composition meets or exceeds a specific temperature which comprises:

a compound comprised of the following structure:

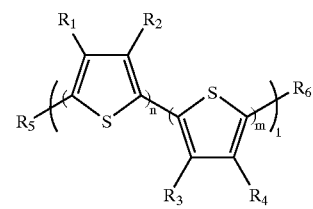

wherein $R_1$–$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted aryl radical or substituted or unsubstituted aryl radical, n is between 1 and 1000,
m is between 0 and 1000, and
1 is between 1 and 1000; and a carrier medium, the compound having a low temperature color and present in the medium in an amount of about 0.05 to about 5.0% by weight based on the total weight of the composition, the structure of the compound designed such that when the composition meets or exceeds the specific temperature, the low temperature color changes to a high temperature color; the change of the low temperature color to the high temperature color commencing within plus or minus 5–10° C. below the specific temperature.

14. The composition of claim 13, wherein the specific design temperature is in the range of between about −40 to 180° C.

15. The composition of claim 14 wherein the specific temperature is any selected temperature within the range.

16. The composition of claim 13 wherein the composition is coated on at least a portion of the surface of the article.

17. The composition of claim 13 wherein the composition is admixed with at least a portion of the article.

18. The composition of claim 13 wherein the composition is coated on and admixed with at least a portion of the article.

19. The composition of claim 13 wherein the medium is selected from the group consisting of polyurethanes; elastomers including polysiloxanes and polydienes; polyacrylates, poly(ethylene terephthalate)s (PET), polysytrenes, polyolefins including polyethylenes (HDPE and LDPE) and polypropylene, polycarbonates, polyacrylics, polyacrylic acids, polyacrylamides, polymethacrylics, polyvinyl ethers, polyvinyl halides, poly(vinyl nitrile)s polyvinyl esters, polyesters, polysofones, polysulfonamides, polyamides, polyimines, polyimides, and carbohydrates.

20. The composition of claim 13 wherein $R_1$ and $R_4$ are —$(CH_2)_{17}CH_3$, $R_2$, $R_3$, $R_5$, and $R_6$ are H, n is 0.8, m is 0.2, and 1 is between 40 and 80, the composition characterized in that a the low temperature color is red a the high temperature color is yellow, and the specific temperature is about 60° C.

21. The composition of claim 13 wherein the compound is present in the medium in an amount of about 0.5% by weight based on the total weight of the composition.

* * * * *